United States Patent
Kuhnert et al.

(10) Patent No.: US 6,290,695 B1
(45) Date of Patent: Sep. 18, 2001

(54) PROCESS AND DEVICE FOR SHAPING SURFACES

(75) Inventors: Jürgen Kuhnert; Holger Mäusezahl, both of Jena; Stefan Pieger, Wendelstein; Eckhard Schroeder, Eckental, all of (DE)

(73) Assignee: Aesculap Meditech GmbH, Jena (DE)

( * ) Notice: Subject to any disclaimer, the term of this patent is extended or adjusted under 35 U.S.C. 154(b) by 0 days.

(21) Appl. No.: 09/269,963

(22) PCT Filed: Oct. 22, 1997

(86) PCT No.: PCT/EP97/05828

§ 371 Date: Apr. 8, 1999

§ 102(e) Date: Apr. 8, 1999

(87) PCT Pub. No.: WO98/18415

PCT Pub. Date: May 7, 1998

(30) Foreign Application Priority Data

Oct. 26, 1996 (DE) ............................................. 196 44 664
Jun. 28, 1997 (DE) ............................................. 197 27 573

(51) Int. Cl.$^7$ .................................................. A61B 18/18
(52) U.S. Cl. ................................. 606/5; 606/11; 606/17; 607/89
(58) Field of Search ............................. 606/4–6, 10–18; 607/88–92; 219/121.6–121.73, 121.78–121.83, 121.85, 121.86

(56) References Cited

U.S. PATENT DOCUMENTS 6,099,522 * 8/2000 Knopp et al. ............................ 606/5

FOREIGN PATENT DOCUMENTS

| 0247260 | 12/1987 | (EP) . |
| 0609978 | 8/1994 | (EP) . |
| 0628298 | 12/1994 | (EP) . |
| 2655837 | 6/1991 | (FR) . |
| WO93/16631 | 9/1993 | (WO) . |
| WO9611655 | 4/1996 | (WO) . |
| WO97/17903 | 5/1997 | (WO) . |

* cited by examiner

*Primary Examiner*—Lee Cohen
*Assistant Examiner*—David M. Ruddy
(74) *Attorney, Agent, or Firm*—Jordan and Hamburg LLP

(57) ABSTRACT

A process and device for shaping surfaces by laser machining and which are used for photorefractive keratectomy and shaping contact lenses. The shaping is performed in stages so that after any interruption in the process, a complete partial correction of the entire surface is obtained. A computing unit receives data from input units and directs data to a block generator which associates laser machining coordinates to enable the removal of individual surface layers. A sequence generator gathers the data generated by the block generator into blocks which correspond to an individual ablation areas, and orders the blocks into sequences. A block sequence transmitted by the sequence generator acts upon a laser beam deflector and beam shaping unit such that the complete partial correction of the surface is obtained for each block sequence. A central processor coordinates control of the laser, the beam shaping unit and the laser beam deflector.

21 Claims, 3 Drawing Sheets

PROCESS AND DEVICE FOR SHAPING SURFACES

BACKGROUND

The invention relates to a process and device for shaping surfaces, in particular lenses, by laser ablation of the surfaces, particularly but not exclusively, surfaces of biological material. The invention preferably is applied in photorefractive keratectomy (PRK) and in ophthalmological precision shaping of contact lenses.

The known state of art will be described hereinafter with reference to processes and devices for shaping surfaces relating to the correction of deficiency of sight and and which are most relevant to the present invention. The ablation processes in the treatment of deficiencies of sight of the human eye which have been carried out since the middle 1980's are all based on formulas for calculating the required flattening and steepening, respectively, of the cornea as first described by Munnerlin. When correcting myopia and according to the above calculation, more corneal tissue is ablated in the center of the cornea than in the peripheral ranges of the cornea. When correcting hyperopia, more tissue is ablated in the periphery of the cornea than in the center of the cornea. The enhanced or reduced effect caused in this manner with respect to the power refraction of the cornea surface corresponds to that of a contact lens.

In previous processes closely related to the present invention, the ablation of a respective amount of cornea is carried out in individual successive ranges of constantly varying areas. In the theoretically simplest case, namely the correction of myopia, the areas are described by successive circles of continuously decreasing or increasing diameters. To obtain an optimal result of treatment, it is necessary to completely ablate all layers in a series. In the presently known procedures, such series are worked off in a continuously increasing or decreasing sequence from the beginning to the end. When, while performing such procedures, there is an unintentional break-off of the treatment, anomalous cornea surfaces will result which generally lead to a considerable deterioration of eyesight. Regrettably, such defects of sight can be removed only partially or not at all by conventional means such as glasses or contact lenses. The only way to correct the situation will be to continue treatment at exactly that point where it was interrupted. When the exact point cannot be found or the patient is not ready to undergo a further treatment, a permanent deterioration of the eyesight will result.

A detailed description of the state of art is disclosed in European Patent Application No. 90308709.6 (corresponding to German Patent Publication No. DE 690 24 558 T2).

U.S. Pat. No. 5,520,679 describes an ophthalmic surgery method using a spot scanning laser in which the cornea ablation is achieved by setting single laser spots. This method, which operates like the ablation processes mentioned hereinbefore, tries to achieve an ablation as uniform as possible by setting laser spots in close timely succession with a defined overlap rate. This, however, involves an increased thermal stress to individual ranges of area, in particular, when an erbium laser is employed.

SUMMARY OF THE INVENTION

It is an object of the present invention to provide a process and device for shaping surfaces, in particular lenses and, more particularly, surfaces of biological material, by using lasers of pulsed laser output beams, which ensure that, at a sudden desired or undesired break-off of the surface shaping, at least an acceptable partial correction of the surface to be shaped is obtained which represents an improvement compared to the initial state.

It is a further object of the invention to substantially reduced the thermal stress of the surface to be shaped, in particular, when employing an erbium laser.

The objects are realized by a device and process for shaping surfaces by laser ablation in which required coordinates of individual laser shots for entirely ablating the surface are determined, the laser shots are associated together into blocks of laser shots, each block including laser shots for ablating an ablation area in a single layer of the surface and then the blocks are combined into block sequences, each block sequence including specific blocks of laser shots effective to achieve a complete partial correction of the entire surface. Control data is generated for controlling a laser deviation unit and a beam formation unit based on the block sequences such that the complete partial correction of the entire surface is obtainable for each block sequence. The laser, the beam formation unit and the laser deviation unit are then controlled to obtain the complete partial correction of the entire surface for each block sequence.

According to the process and device used in accordance with the invention, the individual layers of a surface to be shaped are ablated in a predetermined sequence in order to minimize the risk of a deterioration of eyesight upon an unexpected breaking-off, i.e., interruption, of treatment. Instead of a shaping which, only at the end, provides an optically correct spherical cornea surface including the desired complete correction, the process according to the invention using the device in accordance with the invention produces as many partial corrections of acceptable intermediate results as feasible. Thus, upon a sudden breaking-off of treatment, there never will result severely irregularly shaped surfaces. Though in such a case, the desired complete correction intended by the shaping is not achieved, it is feasible, however, to remove the remaining defect of sight considerably more easily with glasses or contact lenses. Moreover, a new PRK can be carried out with considerably fewer complications at a later time even using devices performing different methods.

The device and the shaping process described herein are adapted to be used with all presently applied PRK-methods, such as area ablation, slit scanning, and small spot scanning, in ablations of the cornea surface as well as in intrastromatic ablations of tissue in connection with the LASIK-method or lasers of the picosecond range.

The process in accordance with the invention differs from the multi-pass method occasionally used with devices operating on the area ablation principle in that the present invention intentionally produces a number of partial corrections which are as small as possible. The multi-pass method typically provides only a division into two to three partial corrections. Moreover, the multi-pass technique tries to reduce certain side-effects typically present for area ablation procedures, such as too strong a drying-out, too strong a heating of tissue, and the development of "Central Islands".

BRIEF DESCRIPTION OF THE DRAWINGS

The invention will be explained in more detail by virtue of the drawings which illustrate one embodiment thereof.

DETAILED DESCRIPTION

Figure 1:
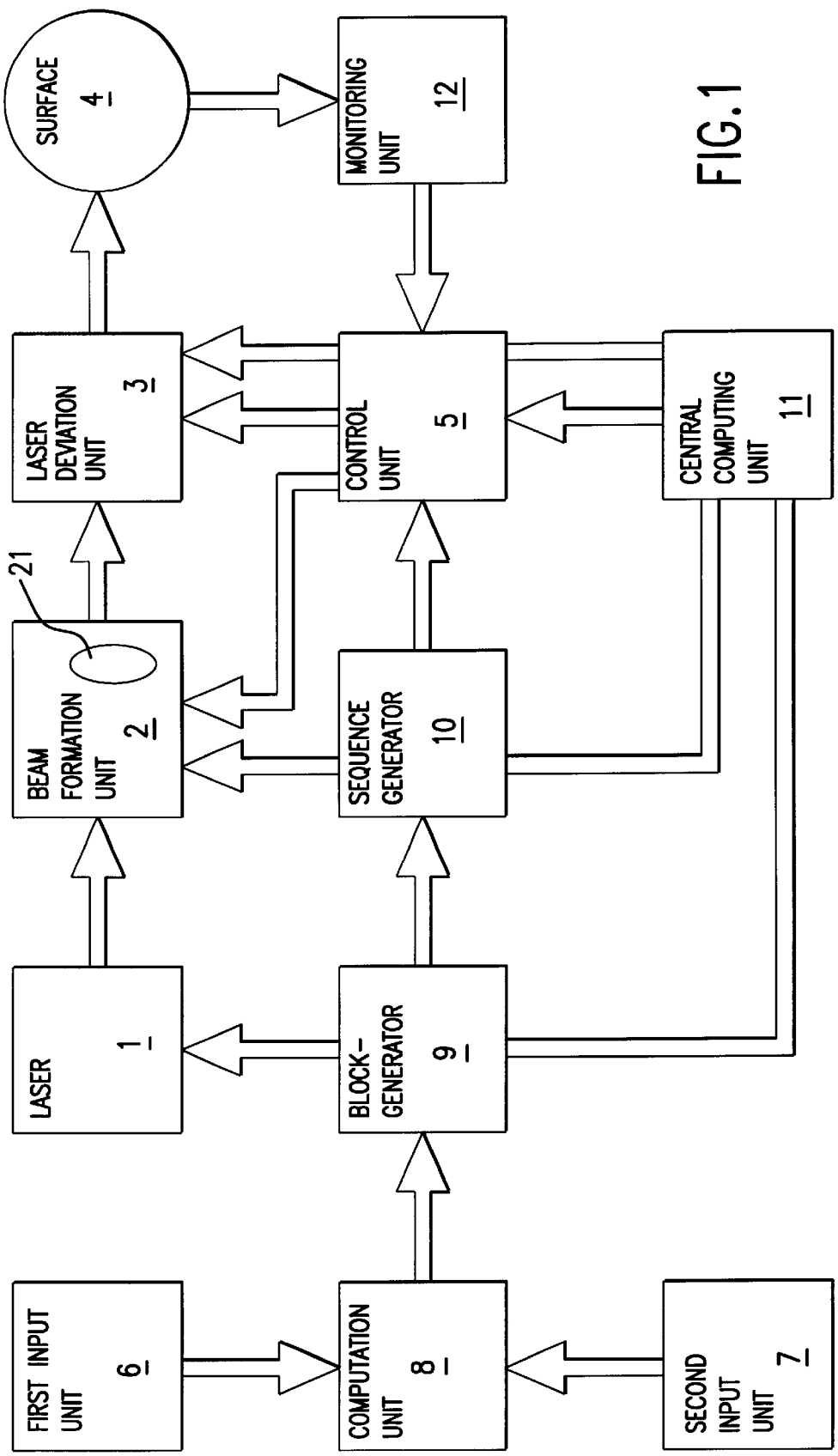
FIG. 1 shows a block diagram of the essential components of the device in accordance with the invention for use in a process in accordance with the invention as well as the operational correlation thereof.

In FIG. 1, the essential components of the device in accordance with the invention are shown in blocks. The device comprises a pulsed laser 1, known in itself, used for laser scanning. For the application in consideration, lasers of pulsed laser output beams, for example, a UV-laser, such as excimer lasers, Er:YAG-lasers, or Q-switch lasers of suitable wavelengths, and intensity and energy, respectively, may be used. The laser 1 is followed by a beam formation unit 2 comprising, as known in the prior art, lenses, reflectors, and prisms. Furthermore, a laser deviation unit 3 is provided, tuned to the laser pulse sequence, which laser deviation unit 3 deviates the laser radiation in a defined manner to a surface 4 to be shaped. The laser deviation unit 3 and the beam formation unit 2 are connected to a control unit 5. A first input unit 6 is provided to drive the control unit 5 in a desired, manner, the refractive input values such as dpt, sph, zyl are fed into the first input unit 6. These starting parameters have to be initially detected in conventional manner, irrespective of the shaping device used in the procedure. Furthermore, a second input unit 7 is provided which is particularly adapted to detect laser relevant data. This data relates to the diameter of the laser beam, the energy density of the laser beam, the energy distribution across the laser beam cross-section, and an overlap factor. The data is variably predetermined, both individually and collectively. Both input units 6, 7 are associated with a computation unit 8 in which all the required coordinates of the single laser shots are correlated to one another in dependence on the entire surface 4 to be ablated. In other words, in computation unit 8, the number of laser spots to be set are detected and determined and the partial areas of the surface to be ablated in dependence on the laser parameters and in which the laser spots have to be set in order to put surface 4 into the desired value state are also detected and determined. The computation unit 8 is followed by a so-called block-generator 9 into which the data from the computation unit 8 is fed. In the block-generator 9, the coordinates of the single laser shots for ablation of any desired preselectable individual surface layer to be ablated (refer to, for example, FIG. 3, any desired area covered by a step x) are related to one another in such a manner (combined into blocks) that laser spots closely succeeding in time in the individual ablation area are set in a mutually spaced sequence such that they do not overlap. Advantageously, this is achieved via a random distribution and involves the advantage, when applying the process, that the thermal stress in the ablation area is minimized. Finally, the block generator 9 is followed by a sequence generator 10 which combines the individual blocks formed in the block generator 9 and generates a sequence underlying the present invention. The sequence represents a block-sequence, each of which corresponds to the partial shaping steps according to FIG. 3 (steps 1 to 6; 7 to 12; 13 to 18; 19 to 24; 25 to 30; 31 to 36; 37 to 42; 43 to 48; 49 to 54). Each of the partial shaping steps represents in itself a complete partial correction. The defined block sequence fed by cooperation of the units mentioned above from the operation sequence 10 into the control unit 5, on the one hand, is adapted to generate control data for controlling control the laser deviation unit 3 and, on the other hand, to control the beam formation unit 2 and, in particular, in the beam formation unit 2, to control an aperture 21 having a variable opening provided in the beam formation unit 2. The operation of the aperture 21 will be explained in more detail in connection with the manner in which the process is performed. Furthermore, a central computing unit 11 is provided which, in dependence on the control data fed out by the control unit 5, coordinates the connection to and the control of at least the laser unit 1, the beam formation unit 2; 21, and the laser deviation unit 3.

Within the scope of the invention, it is possible to associate the first and second input units 6, 7, the computing unit 8, the block generator 9, the sequence generator 10, and the control unit 5 with a second computing unit (not shown) which is connected to the central computing unit 11. It is also feasible to integrate these units in the central computing unit 11.

In addition to the units described above, it is advantageous to provide a monitoring unit 12 which detects accidental outlying motions of the surface 4 to be shaped and transmits respective correction signals based on the detected motions to the laser deviation unit 3 via the control unit 5. Such a monitoring unit is described, for example, in "Corneal surgery by two-dimensionally scanning of a low-energy excimer laser beam" by A. Unkroth et al. in SPIE Vol. 2126 Ophthalmic Technol. IV 1994 pg. 217 ff.

For better understanding of the process in accordance with the invention, first FIG. 2 will be explained which by example, according to the prior art, represents the sequence of the shaping steps required with respect to a myopia correction under application of the so-called small spot scanning.

Figure 2:
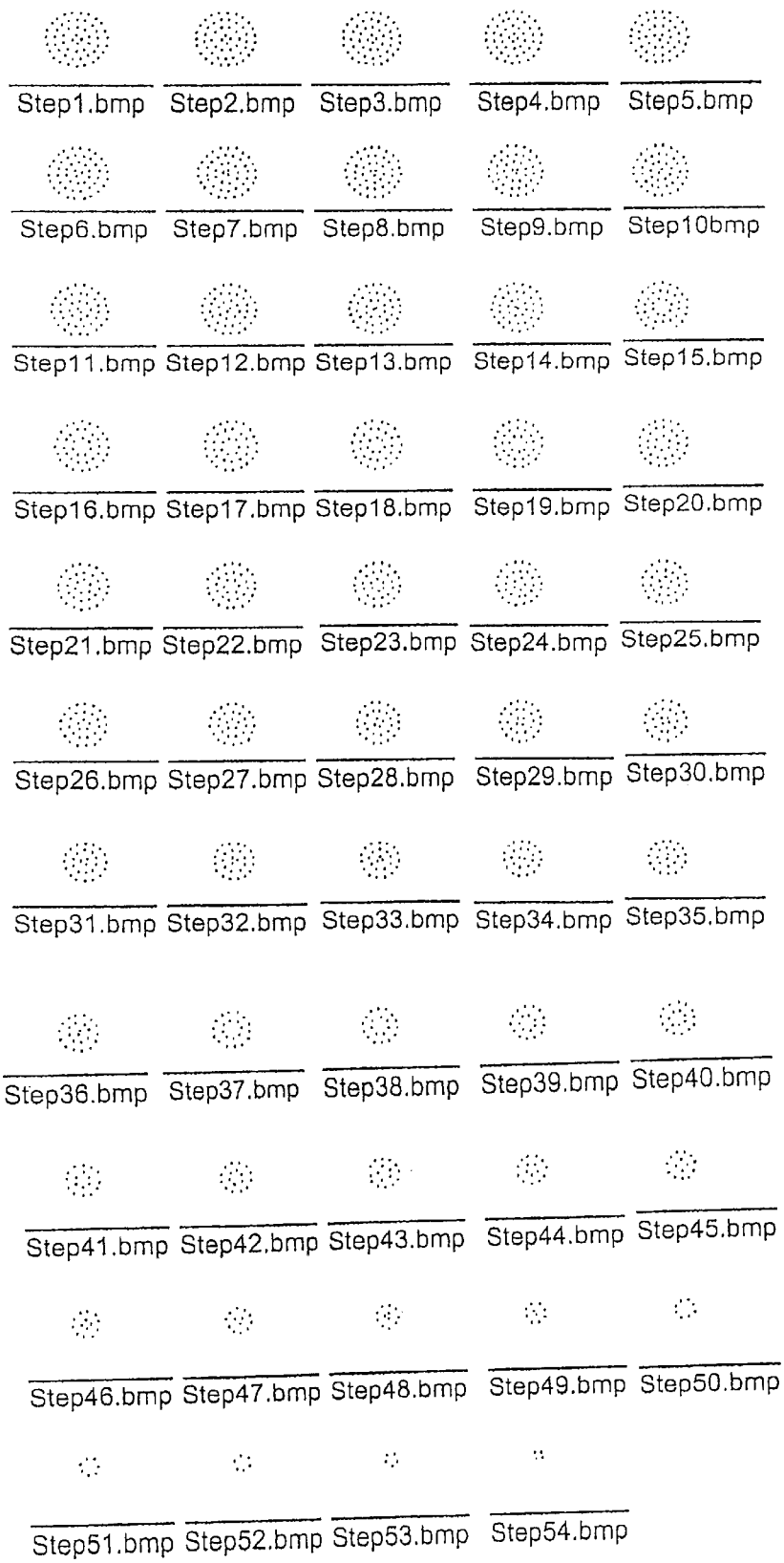
FIG. 2 shows an example of the sequence of operation steps for myopia correction in the case of application in the so-called small spot scanning according to the prior art.

According to FIG. 2, the individual ablation layers are arranged in continuous progression as they will be used for a treatment of spherical myopia in small spot scanning. The individual spots mark the centers of the individual laser ablations of a circular laser beam having a diameter of about 1–2 mm. At a suitable overlap factor and, for example, at a suitable Gaussian beam profile, there will result from all the individual laser shots per layer, one tissue ablation each within an area. The tissue ablation is of any kind as concerns the correction to be produced, however, as refractively uniform as possible. With the Area Ablation Method such an area will correspond to a single laser pulse each. Only when the sequence of, in the example according to FIG. 2, all fifty-four steps is completed, each of which being representative of the ablation of one layer, the desired correction will be achieved with a stronger ablation of tissue in the center. Each break-off of the shaping of the surface before the last shaping step has been completed involves the disadvantages described above.

Figure 3:
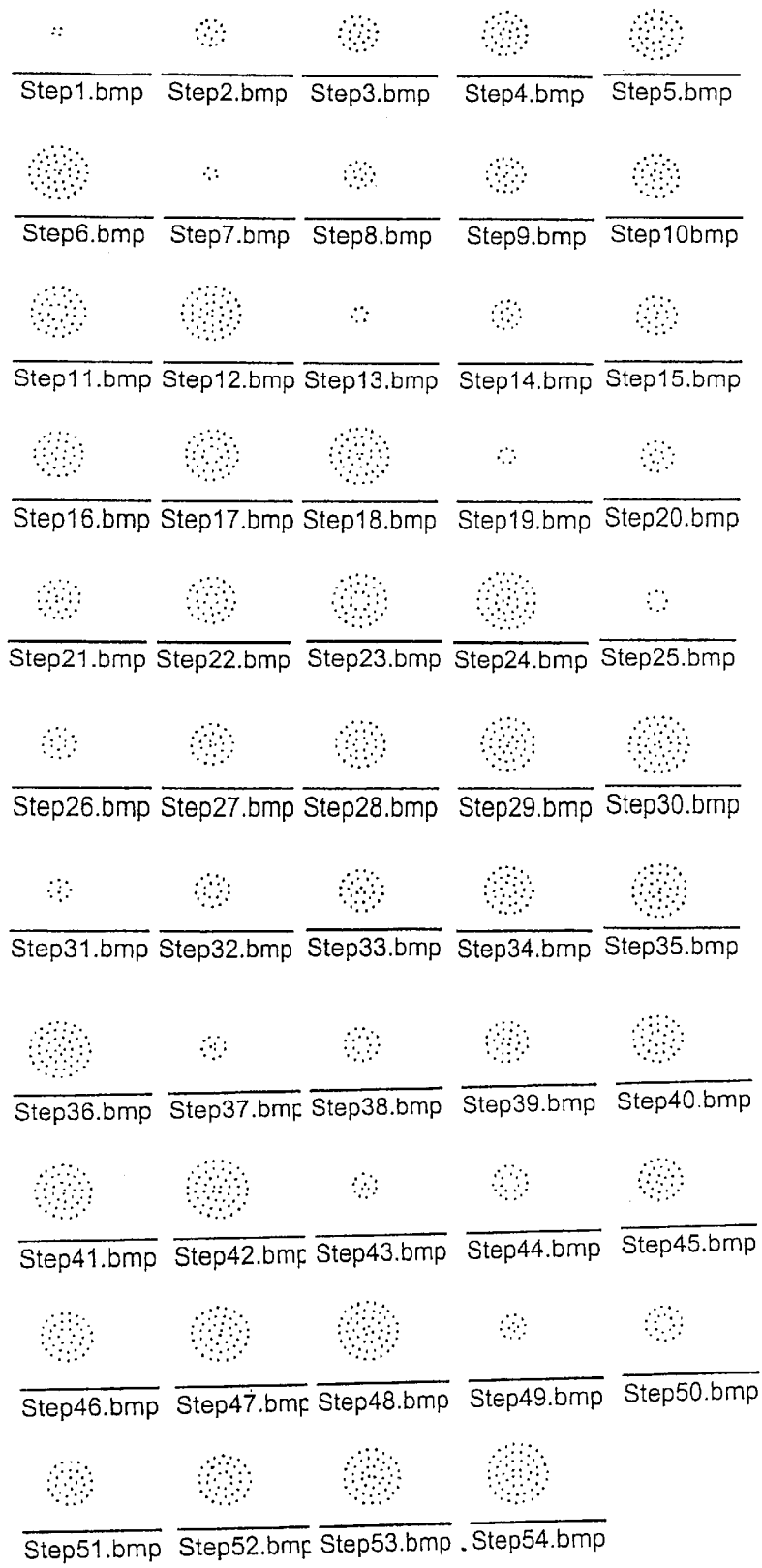
FIG. 3 shows a feasible sequence of the operation steps required for myopia correction in accordance with the invention also in the case of application in the small spot scanning.

In contrast thereto, the process in accordance with the invention will be described by example of a sequence of required shaping steps for myopia correction using the Small Spot Scanning, as shown in FIG. 3. In the same manner as for FIG. 2, the sequence of individual ablation layers applied in the process is represented wherein one respective series of ablations of layers combined according to the invention (refer to steps 1 to 6; 7 to 12; 13 to 18; 19 to 24; 25 to 30; 31 to 36; 37 to 42; 43 to 48; 49 to 54) forms one respective individual partial correction. The precise number of layers per partial correction can be varied in definite ranges. On one hand, in order that a theoretical approximation to a spherical surface is feasible at all, the number of layers should not fall below a minimum number of layers. On the other hand, the refractive effect of the partial correction should be kept as low as possible in order to keep the resulting residual anomalies upon a break-off of treatment to an appropriate low refractive frame.

A minimum number of five layers seems to be suitable just as a determinable maximum number which corresponds to a correction of approximately half a diopter. This would result in, for example, 15 layers at an ablation depth of 9 μm per dpt for a 5 mm myopia treatment and at a typical layer thickness of 0.3 μm.

Using a laser 1 generating a pulsed laser output beam, for example, a UV-laser, such as an excimer laser, an Er:YAG-laser, or a Q-switch laser of suitable wavelengths, and intensity and energy, respectively, suited for the intended application, and using the laser deviating unit 3, which can comprise a controllable oscillating reflector or the like, tuned to the laser pulse sequence, laser spots are set in the area to be shaped in such a manner that there are carried out in relation to the lens profile to be shaped (myopia, hyperopia, astigmatism, cornea scars or the like) and departing from the desired value. The process entails the following steps:

a) in a first preselected area, a plurality of laser spots are set successively and as uniform as feasible in a plane, however, randomly distributed,
  b) in a second area enlarged or diminished compared to the first one, a plurality of individual laser spots are also set similar to the first area with the same measures as under a), however, displaced relative to the individual laser spots of the first area, but in a same or different number,
  c) the process of laser spot setting is continued in n areas, wherein n should be at least 5, under the same measures of a) and b) until the plane of the entire areas to be shaped has been covered for a first time and has been substantially refractively and uniformly ablated,
  d1) in this shaping step, a break-off of the ablation process, if possibly required, takes place, wherein at least one optical partial correction is realized, or
  d2) the shaping steps according to a) to c) are continued until a uniform ablation of the entire area to be shaped and corresponding to the desired value of the surface, is achieved, whereby a refractive, in particular spherical ablation of the surface 4 to be shaped will be obtained.

With reference FIG. 3, it can be seen that in a first step (step 1) four laser spots are set in time sequence according to the measures under a). In other words, after setting the respective actual laser spots, preferably the respective setting of laser spots more remote from the first one is carried out, so that a local overheating due to the setting of several spots in a narrow area is effectively prevented. Advantageously, the control unit 5 permits a partial overlap of preceding ablation areas only for the respective following ablation layers (step 2, . . . ,n). In the second shaping step (step 2) subsequent to step 1, a plurality of laser spots are set in a somewhat larger area, wherein in step 2, the four laser spots centrally set according to step 1 in the example, are already set displaced relative to those of step 1. When considering only the laser spots (refer to steps 3 to 6) set in the central area in accordance with step 1, then it can be seen that also the number of laser spots and their coordinates are varied. This is also true for the further areas surrounding the central one. Therefore, the generated first sequence of ablation layers (steps 1 to 6) yields a first optical partial correction in which according to the measures under d1) a break-off, if possibly necessary, of the shaping process can take place without any disadvantageous effects. Referring again to FIG. 3, it can be seen that upon performing the process, explained by example, up to the last shaping step in the individual block sequences, it becomes obvious that a uniform material ablation is achieved by a continuous variation of both the number and the coordinates of the individual laser spots, wherein a higher ablation is obtained in the central area, since the laser spots have to be set there at each step. Thus, as exemplified, an exact spherical lens correction can be carried out at a respective control of the process.

Furthermore, it is within the scope of the invention that the shaping process is at first carried out at least once with the first parameters. This is done at variations of the laser spot diameter, and/or of the energy density of the laser beam, and/or of the laser spot profile during the execution of the process steps under the measures a) to c) by a respective control of the laser 1 and/or the beam formation unit 2. Subsequent thereto, the process steps according to a) to c) are repeatedly carried out with changed parameters until a shaping state according to the measures d1) which state corresponds to a partial correction will be achieved, or a complete correction according to the measures d2).

Particularly, it is within the scope of the invention to employ laser spots having different spot diameters. It is advantageous to carry out at least one shaping cycle, i.e., steps a) to c), with a large spot diameter of the laser, and subsequent ones with smaller laser spot diameters. The combination of shaping cycles using different laser spot diameters ensures both the realization of short operation times and a shaping ablation according to the desired parameters. When, for example, a laser beam having a diameter of 1 mm is employed for fine ablation, then this could have been preceded at least one time by a shaping ablation according to the measures of a) to c) carried out using a larger laser beam having a diameter of, for example, 2 mm, at least in such areas where a greater shaping ablation amount is required.

In another embodiment, the operation time can be reduced while simultaneously satisfing the desired ablation by inserting a unit between the laser 1 and the surface 4 to be shaped, which unit affects the energy density of the laser radiation. Such a unit can be, for example, a mechanical or a variable optical attenuator. Furthermore, it is within the scope of the invention to carry out at least one shaping cycle a) to c) using a high energy density and subsequent ones using a lower energy density.

The invention is not limited to the embodiments described above. Thus, for example, it is within the scope of the invention that individual ablation areas are formed by closed annular tracks or slit-shaped ablation zones by means of the beam formation unit 2; 21 and/or the beam deviating unit 3 which, by virtue of the ablation process in accordance with the invention, enables lens corrections to be performed at will and departing from the spherical desired value.

The lasers employed in the invention can be those proposed for the PRK and the LASIK-methods, respectively. Preferably, the laser employed is an excimer laser having a wavelength of 193 nm or an ER:YAG laser having a wavelength of 2940 nm. When an excimer laser is employed, the energy density applied to the surface to be shaped amounts to 100–300 mJ/cm$^2$. The laser spot upon the surface 4 to be shaped is substantially circular and exhibits a laser spot diameter of 3 mm for at least one ablation layer. Further layers are ablated with a laser spot diameter of 1 mm. Particularly in this case, the beam profile can exhibit a Gaussian distribution, but a can-shaped distribution is also feasible. It is particularly within the scope of the invention to carry out the large-area ablation using a Gaussian distribution and to employ a can-shaped distribution for the smaller diameter ablations. Such a combination enables a continuous transition to the untreated areas to be obtained and to treat anomalies of the cornea such as, for example, scars.

It is within the scope of the invention to employ the process described above for precisely shaping contact lenses.

LIST OF REFERENCE NUMERALS

1—laser unit
2—beam formation unit
21—aperture
3—laser deviation unit
4—surface to be shaped
5—control unit
6—first input unit
7—second input unit
8—computation unit
9—block generator
10—sequence generator
11—central computing unit
12—monitoring unit

What is claimed is:

1. A device for shaping surfaces by laser ablation, comprising
a pulsed laser:
a beam formation unit;
a laser deviation unit tuned to a pulse sequence of the laser for deviating the laser beam to a surface to be shaped:
a control unit for controlling said laser deviation unit and said beam formation unit;
a first input unit containing starting parameters for shaping the surface:
a second input unit containing data relating to the laser;
a computation unit arranged to receive the starting parameters from said first input unit and laser data from said second input unit, said computation unit correlating required coordinates of individual laser shots for the surface to be entirely ablated;
a block generator arranged to receive the coordinates of the laser shots from said computation unit, said block generator associating the laser shots together into blocks of laser shots, each of the blocks including laser shots for ablating an ablation area in a single layer of the surface;
a sequence generator coupled to said block generator for receiving the blocks generated in said block generator, said sequence generator combining said blocks into block sequences, each of the block sequences including specific blocks of laser shots effective to achieve a complete partial correction of the entire surface by ablating a complete surface layer;
said control unit being arranged to receive the block sequences from said sequence generator and generate control data for controlling said laser deviation unit and said beam formation unit based on the block sequences such that the complete partial correction of the entire surface is obtainable for each of the block sequence; and
a central computing unit arranged to receive the control data from said control unit and control said laser, said beam formation unit and said laser deviation unit to obtain the complete partial correction of the entire surface for each of the block sequences.

2. The device as claimed in claim 1, wherein said beam formation unit includes at least one element arranged to vary at least one of the size, energy density and profile of the laser spot upon the surface being shaped.

3. The device as claimed in claim 2, wherein said at least one element in said beam formation unit is an aperture.

4. The device as claimed in claim 2, wherein said at least one element in said beam formation unit is an attenuator.

5. The device as claimed in claim 1, further comprising a monitoring unit coupled to said control unit and arranged to detect accidental outlying motions of the surface being shaped and transmit correction signals to said laser deviation unit via said control unit based on the motions detected by said monitoring unit.

6. The device as claimed in claim 1, wherein said first input unit, said second input unit, said computing unit, said block generator, said sequence generator, and said control unit are associated with an additional computing unit connected to said central computing unit.

7. The device as claimed in claim 1, wherein said first input unit, said second input unit, said computing unit, said block generator, said sequence generator, and said control unit are integrated in said central computing unit.

8. A process for shaping surfaces by laser ablation, comprising the steps of:
a) setting a plurality of laser spots in a first preselected area of the surface,
b) setting a plurality of laser spots in a second area of the surface having a different size than the first area, the laser spots in the second area being displaced relative to the laser spots in the first area,
c) continuing the process of laser spot setting in additional areas until laser spots are set in at least five areas and the surface is covered and has been substantially refractively and uniformly ablated,
d1) optionally stopping the shaping process whereby at least one optical partial correction is realized by the set laser spots, and
d2) continuing the shaping steps according to steps a) to c) until a uniform ablation of the entire area to be shaped and having a desired shape is achieved.

9. The process as claimed in claim 8, further comprising the step of setting laser spots close together in time in mutually spaced relation so that overlap of the ablation areas generated per laser spot does not occur.

10. The process as claimed in claim 8, further comprising the step of subjecting partial areas of the surface are subject to multiple laser spot ablation within a shaping cycle of steps a) to c).

11. The process as claimed in claim 8, further comprising the step of varying at least one of a diameter of the laser spot, energy density of the laser beam and a profile of the laser spot during steps a) to c) by controlling at least one of the laser and a beam formation unit associated with the laser.

12. The process as claimed in claim 8, further comprising the steps of:
performing steps a) to c) using a larger laser beam spot diameter in areas where a greater ablation amount is required, and then
performing steps a) to c) at least one additional time using a smaller laser beam diameter.

13. The process as claimed in claim 8 or 10, further comprising the step of forming individual ablation areas by closed annular tracks by means of at least one of a beam formation unit associated with the laser and a laser beam deviating unit associated with the laser.

14. The process as claimed in claim 8 or 10, further comprising the step of forming individual ablation areas by slit-shaped ablation zones by means of at least one of a beam formation unit associated with the laser and a laser beam deviating unit associated with the laser.

15. The device as claimed in claim 1, wherein the data relating to the laser contained in said second input unit is at least one of the laser beam diameter, the energy density, energy distribution, and an admissible overlap factor for individual laser spots.

16. The device as claimed in claim 1, wherein the surface is a lens.

17. The process as claimed in claim 8, wherein the laser spots are set in the areas successively and uniformly in a plane, and randomly distributed in the plane.

18. A process for shaping surfaces by laser ablation, comprising the steps of:
   determining required coordinates of individual laser shots for entirely ablating the surface;
   associating the laser shots together into blocks of laser shots, each of the blocks including laser shots for ablating an ablation area in a single layer of the surface;
   combining the blocks into block sequences, each of the block sequences including specific blocks of laser shots effective to achieve a complete partial correction of the entire surface by ablating a complete surface layer; and
   controlling the laser, a beam formation unit and a laser deviation unit based on the block sequences to obtain the complete partial correction of the entire surface for each of the block sequences.

19. The process as claimed in claim 18, wherein the step of controlling the laser, the beam formation unit and the beam deviation unit comprises the step of generating control data for controlling the laser deviation unit and the beam formation unit based on the block sequences such that the complete partial correction of the entire surface is obtainable for each block sequence.

20. The process as claimed in claim 18, further comprising the steps of:
   detecting accidental outlying motions of the surface being shaped; and
   transmitting correction signals to the laser deviation unit based on the detected motions.

21. The process as claimed in claim 18, further comprising the step of varying at least one of a diameter of the laser spots, energy density of the laser beam and a profile of the laser spot by controlling at least one of the laser and the beam formation unit.

* * * * *